United States Patent [19]

Berkoff et al.

[11] 3,976,633

[45] Aug. 24, 1976

[54] SUBSTITUTED CYANO,TRIFLUOROMETHYLPHENYL LINEAR TRIAZENES

[75] Inventors: Charles E. Berkoff, Huntingdon Valley; David T. Hill, North Wales; Bernard Loev, Broomall, all of Pa.

[73] Assignee: SmithKline Corporation, Philadelphia, Pa.

[22] Filed: June 3, 1974

[21] Appl. No.: 475,699

[52] U.S. Cl. ............................ 260/140 R; 260/141; 260/578; 424/226
[51] Int. Cl.² ............... C07C 115/00; A61K 31/655
[58] Field of Search ................... 260/140; 424/226

[56] References Cited
UNITED STATES PATENTS

| | | |
|---|---|---|
| 3,299,038 | 1/1967 | Tomcufcik et al. ................ 260/140 |
| 3,382,061 | 5/1968 | Bondarenko et al. .......... 260/140 X |
| 3,526,479 | 9/1970 | Rey et al. ......................... 260/140 X |
| 3,715,435 | 2/1973 | Harnish et al. ..................... 424/226 |
| 3,786,131 | 1/1974 | Buchel et al. ....................... 424/304 |
| 3,839,564 | 10/1974 | Wright et al. ...................... 424/226 |

*Primary Examiner*—Floyd D. Higel
*Assistant Examiner*—John J. Doll
*Attorney, Agent, or Firm*—Janice E. Williams; Joan S. Keps; William H. Edgerton

[57] ABSTRACT

The compounds of this invention are substituted cyano,trifluoromethylphenyl linear triazenes having pharmacological activity. In particular, these compounds have anorectic and anti-obesity activity. A preferred compound is 1,3-bis(2-cyano-5-trifluoromethylphenyl)triazene.

6 Claims, No Drawings

SUBSTITUTED CYANO,TRIFLUOROMETHYLPHENYL LINEAR TRIAZENES

This invention relates to new substituted 1,3-diphenyltriazenes which have pharmacological activity. More specifically, the compounds of this invention have anorectic and anti-obesity activity.

The compounds of this invention are represented by the following structural formula:

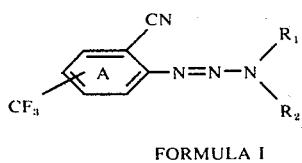

FORMULA I in which:

$R_1$ is phenyl, 4-carboxyphenyl or

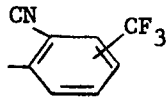

and $R_2$ is hydrogen, formyl, haloacetyl, lower alkanoyl, lower alkoxycarbonyl, lower alkoxycarbonyl(lower)alkanoyl, carboxy(lower)alkanoyl, cycloalkylcarbonyl, N-(lower alkyl)-carbamoyl, N,N-(di-lower alkyl)carbamoyl, N-phenylcarbamoyl, N-(lower alkoxycarbonyl)carbamoyl or N,N-(di-lower alkyl)-amino(lower)alkanoyl.

Advantageous compounds of this invention are represented by Formula I in which $R_2$ is hydrogen, α-chloroacetyl acetyl, ethoxycarbonyl, 3-methoxycarbonylpropionyl, N-methylcarbamoyl, N-propylcarbamoyl, N-phenylcarbamoyl or N-ethoxycarbonylcarbamoyl.

Preferred compounds of this invention are represented by Formula I in which $R_1$ is 2-cyano-4-trifluoromethylphenyl or 2-cyano-5-trifluoromethylphenyl, the trifluoromethyl group of ring A is in the 4- or 5-position and $R_2$ is hydrogen or acetyl.

A particularly preferred compound of this invention is 1,3-bis(2-cyano-5-trifluoromethylphenyl)triazene.

As used herein, the terms "lower alkyl" and "lower alkoxy" denote groups having from one to four carbon atoms, "lower alkanoyl" denotes groups having from two to five carbon atoms, and "cycloalkyl" refers to groups having five or six carbon atoms.

The substituted 1,3-diphenyltriazenes of Formula I where $R_2$ is hydrogen are prepared by coupling of an aniline diazonium ion of the formula

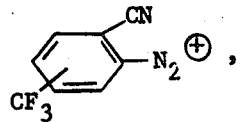

formed for example by treatment of the corresponding aniline with sodium nitrite in 50% aqueous sulfuric acid, with excess amounts of aniline, p-aminobenzoic acid or an aniline of the formula

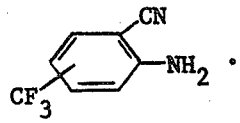

The reaction is carried out, preferably, at 0°C. for from about 15 minutes to about four hours. The product triazenes are isolated and purified by standard methods including solvent extraction and crystallization.

The cyanotrifluoromethylanilines are either known or are prepared by standard synthetic methods as exemplified herebelow.

When $R_2$ is formyl, the compounds of Formula I are prepared by reaction of a 1,3-diphenyltriazene with a mixed anhydride of formic acid and an organic acid, for example acetic acid. The reaction is preferably carried out in a solvent such as ether at 0°C. for about 1 hour.

When $R_2$ is haloacetyl, lower alkanoyl, cycloalkylcarbonyl, lower alkoxycarbonyl, lower alkoxycarbonyl(lower)-alkanoyl or N,N-(di-lower alkyl)carbamoyl, the compounds of Formula I are, preferably, prepared by reaction of a 1,3-diphenyltriazene with an acid halide, preferably chloride, ($R_3COX$ where $R_3$ is halomethyl, lower alkyl or cycloalkyl and X is halo); an alkyl haloformate, preferably chloroformate, ($R_4OCOX$ where $R_4$ is lower alkyl and X is halo); an alkoxycarbonylalkanoyl halide, preferably chloride, ($R_5OCO(CH_2)_nCOX$ where $R_5$ is lower alkyl, $n$ is one to four and X is halo); or a carbamoyl halide, preferably chloride, ($R_6NCOX$ where $R_6$ is di-lower alkyl and X is halo). This reaction is carried out in the presence of a base such as sodium hydride in an inert solvent such as ether at from about 0°C. to the reflux temperature of the solvent, ambient temperature being preferable, for from about 1 to about 24 hours.

The compounds of Formula I where $R_2$ is lower alkanoyl or cycloalkylcarbonyl are also prepared by treatment of a 1,3-diphenyltriazene with an acid anhydride ($R_7CO$—$O$—$COR_7$ where $R_7$ is lower alkyl or cycloalkyl) in the presence of a base such as pyridine, preferably at ambient temperature, or by reaction of the 1,3-diphenyltriazene with a mixed anhydride in a solvent such as ether, preferably at about 0°C.

Alternatively, when $R_2$ is lower alkanoyl such as isobutyryl, propionyl or acetyl, the corresponding compounds of Formula I may be prepared by treatment of a 1,3-diphenyltriazene with an appropriate ketene in a solvent such as ether, preferably at about 0°C.

When $R_2$ is acetyl, the corresponding compounds of Formula I may also be directly obtained from reaction of an acetanilide salt, for example a sodium salt, with the aniline diazonium ion used to prepare the compounds of Formula I where $R_2$ is hydrogen, preferably as the tetrafluoroborate salt.

The compounds of Formula I where $R_2$ is N-(lower alkyl)carbamoyl, N-phenylcarbamoyl or N-(lower alkoxycarbonyl)-carbamoyl are prepared by the reaction of a 1,3-diphenyltriazene with an isocyanate ($R_8NCO$ where $R_8$ is lower alkyl, phenyl or lower alkoxycarbonyl) according to known procedures. For example, the reaction is carried out in a solvent such as ether at from about 0°C. to the reflux temperature of the solvent, ambient temperature being preferred, for from about 2 to 72 hours, preferably 12 hours.

When $R_2$ is N,N-di-(lower alkyl)amino(lower)alkanoyl, the corresponding compounds of Formula I are prepared by reaction of a 1,3-diphenyltriazene with a ω-dialkylamino carboxylic acid or its corresponding salt ($R_9N—(CH_2)_n—CO_2H$ where $R_9$ is di-lower alkyl and $n$ is one to four), for example, in the presence of a dehydrating agent such as N,N-dicyclohexylcarbodiimide in a solvent such as methylene chloride at ambient temperature for about 12 hours. These compounds may also be prepared by reaction of a 1,3-diphenyltriazene with a ω-bromo acid chloride (Br—$(CH_2)_n$—COCl where $n$ is one to four) followed by treatment of the product 3-(ω-bromoalkanoyl)-1,3-diphenyltriazene with a dialkylamine.

The compounds of Formula I where $R_2$ is carboxy(-lower)-alkanoyl are prepared by reaction of a 1,3-diphenyltriazene with a di-acid halide, preferably chloride, (XOC—$(CH_2)_n$—COX where $n$ is one to four and X is halo) in the presence of a base such as sodium hydride in a solvent such as ether, preferably at ambient temperature for about 12 hours, followed by hydrolysis of the resulting 3-(ω-halocarbonylalkanoyl)-1,3-diphenyltriazene.

The anorectic and anti-obesity activities of the compounds of this invention are demonstrated by a standard pharmacological procedure described herebelow. Rats are trained to eat in a 5 hour interval each day over a 2 week period. The test compound is administered orally and food is presented 1 hour later and left in the cages for 5 hours. Food consumption is measured after 1 and 5 hours of feeding. The test is continued each day for 5 days and the rats are weighed daily. At the end of the test, daily food consumptions and body weight changes over the five days for treated rats are compared to controls. Anorectic activity is shown by reduction in one or 5-hour food consumption and anti-obesity activity is shown by loss in body weight over the 5-day test period.

In the above test procedures, the compounds represented by Formula I produce anorexia and anti-obesity activity when administered orally to rats at daily doses of from 6.25 mg./kg. to 100 mg./kg.

Pharmaceutical compositions having anorectic and anti-obesity activity which comprise a pharmaceutical carrier and a compound of Formula I and methods of producing anorexia and anti-obesity activity by administering internally to an animal in an amount sufficient to produce said activity a compound of Formula I are also objects of this invention.

The compounds are preferably administered orally in conventional dosage unit forms, preferably as a capsule, tablet, solution or suspension. Preferably, each dosage unit will contain the active medicament in an amount of from about 25 mg. to about 300 mg. Advantageously, equal doses will be administered two to four times daily with the daily dosage regimen being about 50 mg. to about 1200 mg.

The pharmaceutical compositions are prepared by incorporating a compound of Formula I with a pharmaceutical carrier by standard procedures.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, sesame oil, propylene glycol and the like. Similarly the carrier or diluent can include any time delay material well known to the art, such as glyceryl monostearate or glyceryl distearate alone or with a wax.

A wide variety of pharmaceutical forms can be employed. Thus, if a solid carrier is used the preparation can be tableted, placed in a hard gelatin capsule in powder or pellet form, or in the form of a troche or lozenge. The amount of solid carrier will preferably be about 25 mg. to about 1 g. If a liquid carrier is used, the preparation will be in the form of a syrup, emulsion, soft gelatin capsule or a liquid suspension.

The pharmaceutical compositions are prepared by conventional techniques involving procedures such as mixing, granulating and compressing or dissolving the ingredients as appropriate to the desired preparation.

The following examples illustrate the preparation of the compounds of this invention, but are not to be construed as limiting the scope thereof. Temperatures are in degrees Centigrade (°C.) unless otherwise indicated.

EXAMPLE 1

To 8.9 g. (0.048 mol.) of 2-cyano-5-trifluoromethylaniline is added with cooling (ice bath) a mixture of 10.6 ml. of water and 10.6 ml. of concentrated sulfuric acid. The slurry is stirred until homogeneous, then a solution of 1.66 g. (0.024 mol.) of sodium nitrite in 10.6 ml. of water is added dropwise over a 30 minute period and stirring is continued for 15 minutes. The ice bath is removed and the reaction mixture stirred an additional hour. Water is added to the semi-solid mixture and the slurry is poured into 500 ml. of water. The solid is collected by filtration, washed with water and recrystallized from hot ethanol to give 1,3-bis(2-cyano-5-trifluoromethylphenyl)triazene, m.p. 183°–184°.

EXAMPLE 2

When an equivalent amount of 2-cyano-4-trifluoromethylaniline is substituted in the procedure of Example 1 for 2-cyano-5-trifluoromethylaniline, 1,3-bis(2-cyano-4-trifluoromethylphenyl)triazene, m.p. 194°–195°, is obtained.

EXAMPLE 3

To 21 g. of dry pyridine is added slowly with stirring 23 g. (0.26 mol.) of cuprous cyanide. The mixture rapidly solidifies and is then heated to 125°. Excess pyridine is boiled off and the temperature is decreased to 110°. 3-Amino-2-bromobenzotrifluoride (48 g., 0.20 mol.) is added with stirring and the reaction mixture is heated to 165°–170° for 75 minutes. The mixture is then cooled to 90° and a solution of 75 g. (1.05 mol.) of sodium cyanide in 75 ml. of water is added followed by 250 ml. of benzene. The resulting mixture is stirred for one hour, the layers are separated and the benzene layer is washed with water, dried and evaporated to give 2-cyano-3-trifluoromethylaniline.

Substitution of an equivalent amount of 2-cyano-3-trifluoromethylaniline in the procedure of Example 1 for 2-cyano-5-trifluoromethylaniline gives 1,3-bis(2-cyano-3-trifluoromethylphenyl)triazene.

EXAMPLE 4

2-Bromo-4-nitro-6-trifluoromethylaniline (14.2 g., 0.05 mol.) is dissolved in 300 ml. of acetic anhydride. A catalytic amount of sulfuric acid is added and the reaction mixture is stirred at 25° for 1 hour. The mixture is poured into water and the product 2'-bromo-4'- nitro-6'-trifluoromethylacetanilide is collected by filtration.

Hydrogenation of 2'-bromo-4'-nitro-6'-trifluoromethylacetanilide in ethanol over Raney nickel gives 4'-amino-2'-bromo-6'-trifluoromethylacetanilide which is converted to the sulfate salt by addition of sulfuric acid.

To a suspension of 4'-amino-2'-bromo-6'-trifluoromethylacetanilide sulfate is added two molar equivalents of ethyl nitrite. The reaction mixture is cooled (0°) and stirred for 2 hours then allowed to warm to 25° and a catalytic amount of copper bronze is added. The mixture is stirred for 3 hours with the temperature maintained below 40°. The mixture is then refluxed briefly and cooled. Addition of water gives 2'-bromo-6'-trifluoromethylacetanilide which is collected by filtration.

2'-Bromo-6'-trifluoromethylacetanilide in 50% aqueous sulfuric acid is warmed on a steam bath for 2 hours, then refluxed for 1 hour. Cooling and dilution with water gives 2-bromo-6-trifluoromethylaniline.

2-Bromo-6-trifluoromethylaniline (12.0 g., 0.05 mol.) and 4.5 g. (0.05 mol.) of cuprous cyanide in 100 ml. of dimethylformamide is refluxed for 12 hours. The reaction mixture is decomposed by addition of aqueous ferrous sulfate solution, ether is added, the layers are separated and the ethereal phase is washed with water, dried (MgSO$_4$) and concentrated to give 2-cyano-6-trifluoromethylaniline.

When an equivalent amount of 2-cyano-6-trifluoromethylaniline is substituted in the procedure of Example 1 for 2-cyano-5-trifluoromethylaniline, 1,3-bis(2-cyano-6-trifluoromethylphenyl)triazene is obtained.

EXAMPLE 5

A mixture of 10.2 ml. (0.05 mol.) of acetic anhydride and 4.3 ml. of 98% formic acid is heated to 50° for 2 hours. The mixture is cooled to 0° (ice bath) and a solution of 18.6 g. (0.05 mol.) of 1,3-bis(2-cyano-5-trifluoromethylphenyl)triazene in ether is added dropwise. The reaction mixture is stirred for 30 minutes then the solid product is collected by filtration and washed with water and cold ether to give 3-formyl-1,3-bis(2-cyano-3-trifluoromethylphenyl)triazene.

EXAMPLE 6

A. A solution of 5.6 g. (0.015 mol.) of 1,3-bis(2-cyano-5-trifluoromethylphenyl)triazene in 450 ml. of warm ether is added dropwise to a slurry of 1.20 g. (0.025 mol.) of 50% sodium hydride in 15 ml. of ether. Upon cessation of gas evolution, 1.42 g. (0.018 mol.) of acetyl chloride is gradually added and the reaction mixture is stirred for two hours at 25°. The mixture is filtered to remove excess sodium hydride and the filtrate is concentrated to give 3-acetyl-1,3-bis(2-cyano-5-trifluoromethylphenyl)triazene, m.p. 111°–112° (hexane).

B. Alternatively, 3-acetyl-1,3-bis(2-cyano-5-trifluoromethylphenyl)triazene is prepared by addition of 25 ml. of acetic anhydride to a solution of 5.0 g. (0.013 mol.) of 1,3-bis(2-cyano-5-trifluoromethylphenyl)triazene in 65 ml. of pyridine. The reaction mixture is stirred at 25° for twelve hours, then it is poured into water. The aqueous mixture is extracted with ether, the layers are separated and the ether phase is washed with water, 5% aqueous sodium bicarbonate and water, dried (MgSO$_4$) and concentrated to give 3-acetyl-1,3-bis(2-cyano-5-trifluoromethylphenyl)triazene.

By the same procedure, 3-acetyl-1,3-bis(2-cyano-4-trifluoromethylphenyl)triazene, m.p. 140°–141°, is prepared from 1,3-bis(2-cyano-4-trifluoromethylphenyl)triazene and acetic anhydride.

EXAMPLE 7

Substitution of an acid chloride listed below:
propionyl chloride
butyryl chloride
valeryl chloride
cyclohexylcarbonyl chloride
cyclopentylcarbonyl chloride
in procedure A of Example 6 for acetyl chloride gives the following compounds of this invention, respectively:
3-propionyl-1,3-bis(2-cyano-5-trifluoromethylphenyl)triazene
3-butyryl-1,3-bis(2-cyano-5-trifluoromethylphenyl)triazene
3-valeryl-1,3-bis(2-cyano-5-trifluoromethylphenyl)triazene
3-cyclohexylcarbonyl-1,3-bis(2-cyano-5-trifluoromethylphenyl)-triazene
3-cyclopentylcarbonyl-1,3-bis(2-cyano-5-trifluoromethylphenyl)-triazene.

EXAMPLE 8

When an alkyl chloroformate listed below:
methyl chloroformate
ethyl chloroformate
propyl chloroformate
butyl chloroformate
is substituted in procedure A of Example 6 for acetyl chloride, the following compounds of this invention are obtained, respectively:
3-methoxycarbonyl-1,3-bis(2-cyano-5-trifluoromethylphenyl)-triazene
3-ethoxycarbonyl-1,3-bis(2-cyano-5-trifluoromethylphenyl)-triazene, m.p. 88°–90°
3-propoxycarbonyl-1,3-bis(2-cyano-5-trifluoromethylphenyl)-triazene
3-butoxycarbonyl-1,3-bis(2-cyano-5-trifluoromethylphenyl)-triazene.

EXAMPLE 9

A mixture of 2.0 g. (5.2 mmol.) of 1,3-bis(2-cyano-5-trifluoromethylphenyl)triazene and 1.6 ml. of phenyl isocyanate in 20 ml. of ether is stirred at 25° for 48 hours. The precipitate is collected and recrystallized from ether to give 3-(N-phenylcarbamoyl)-1,3-bis(2-cyano-5-trifluoromethylphenyl)-triazene, m.p. 157°–158°.

EXAMPLE 10

A solution of 0.38 g. (6.7 mmol.) of methyl isocyanate in 20 ml. of ether is added dropwise to 1.6 g. (4.2 mmol.) of 1,3-bis(2-cyano-5-trifluoromethylphenyl)-triazene in 125 ml. of ether. The reaction mixture is stirred at 25° for 12 hours, refluxed for 6 hours, then left to stand at 25° for 48 hours. Removal of the solvent under reduced pressure gives 3-(N-methylcarbamoyl)-1,3-bis(2-cyano-5-trifluoromethylphenyl)triazene, m.p. 170° (dec.).

EXAMPLE 11

To a solution of 5.4 g. (0.014 mol.) of 1,3-bis(-2cyano-5-trifluoromethylphenyl)triazene in 500 ml. of ether is added 15 ml. of propyl isocyanate. The reaction mixture is stirred at 25° for 24 hours after which time the precipitated product is collected by filtration and washed with ether to give 3-(N-propylcarbamoyl)-1,3-bis(2-cyano-5-trifluoromethylphenyl)triazene, m.p. 138°–140° (dec.).

EXAMPLE 12

When an equivalent amount of ethyl isocyanate is used in the procedure of Example 11 for propyl isocyanate, there is prepared 3-(N-ethylcarbamoyl)-1,3-bis(2-cyano-5-trifluoromethylphenyl)triazene.

Similarly, use of butyl isocyanate in place of propyl isocyanate in Example 11 gives 3-(N-butylcarbamoyl)-1,3-bis(2-cyano-5-trifluoromethylphenyl)triazene.

EXAMPLE 13

When 1,3-bis(2-cyano-5-trifluoromethylphenyl)triazene is reacted with dimethylcarbamoyl chloride or diethylcarbamoyl chloride and sodium hydride as described in procedure A of Example 6, the products are, respectively, 3-(N,N-dimethylcarbamoyl)-1,3-bis(2-cyano-5-trifluoromethylphenyl)triazene and 3-(N,N-diethylcarbamoyl)-1,3-bis(2-cyano-5-trifluoromethylphenyl)triazene.

EXAMPLE 14

To a solution of 5.0 g. (0.013 mol.) of 1,3-bis(2-cyano-5-trifluoromethylphenyl)triazene in 500 ml. of ether is added 3.0 g. (0.026 mol.) of ethoxycarbonyl isocyanate. The reaction mixture is stirred at 25° for 48 hours after which time the product is collected by filtration and washed with ether to give 3-[(N-ethoxycarbonyl)carbamoyl]-1,3-bis(2-cyano-5-trifluoromethylphenyl)triazene, m.p. 151°–152°.

EXAMPLE 15

When an equivalent amount of methoxycarbonyl isocyanate is used in place of ethoxycarbonyl isocyanate in the procedure of Example 14, the product is 3-[(N-methoxycarbonyl)carbamoyl]-1,3-bis(2-cyano-5-trifluoromethylphenyl)triazene.

EXAMPLE 16

Oxalyl chloride (25.0 g., 0.2 mol.) is added to a suspension of 16.4 g. (0.14 mol.) of butyl carbamate in 75 ml. of chloroform. After cessation of gas evolution, the reaction mixture is refluxed in a nitrogen atmosphere for 12 hours. The mixture is cooled, filtered and the filtrate is distilled in vacuo to give butoxycarbonyl isocyanate.

Substitution of an equivalent amount of butoxycarbonyl isocyanate in the procedure of Example 14 for ethoxycarbonyl isocyanate gives 3-[(N-butoxycarbonyl)carbamoyl]-1,3-bis(2-cyano-5-trifluoromethylphenyl)triazene.

EXAMPLE 17

When propyl carbamate is reacted with oxalyl chloride as described in the procedure of Example 13, propoxycarbonyl isocyanate is obtained.

Substitution of an equivalent amount of propoxycarbonyl isocyanate in the procedure of Example 14 for ethoxycarbonyl isocyanate gives 3-[(N-propoxycarbonyl)carbamoyl]-1,3-bis(2-cyano-5-trifluoromethylphenyl)triazene.

EXAMPLE 18

A solution of 3.5 g. (0.05 mol.) of dimethylketene in ethyl acetate is added dropwise under a nitrogen atmosphere to a cooled (0°) solution of 18.6 g. (0.05 mol.) of 1,3-bis(2-cyano-5-trifluoromethylphenyl)triazene in ether. The reaction mixture is stirred for 12 hours then concentrated at reduced pressure. Crystallization of the residue from ether gives 3-isobutyryl-1,3-bis(2-cyano-5-trifluoromethylphenyl)triazene.

EXAMPLE 19

A cooled solution of 3.6 ml. of concentrated sulfuric acid and 3.6 ml. of water is added to 3.0 g. (0.016 mol.) of 2-cyano-5-trifluoromethylaniline. The slurry is cooled (ice bath) and stirred and a solution of 1.1 g. (0.016 mol.) of sodium nitrite in 6 ml. of water is added dropwise. The resulting mixture is then added to a solution of 3 ml. of aniline in 120 ml. of ethanol. Additional aniline (6 ml.) is added and the reaction mixture is stirred for 15 minutes. The mixture is poured into 500 ml. of water and the precipitate is collected by filtration, washed with water and recrystallized from hexane to give 3-(2-cyano-5-trifluoromethylphenyl)-1-phenyltriazene, m.p. 139°–141°.

EXAMPLE 20

A solution of 10.0 g. (0.026 mol.) of 1,3-bis(2-cyano-5-trifluoromethylphenyl)triazene and 1.8 g. (0.037 mol.) of 50% sodium hydride in ether is added to a solution of 3.2 g. (0.028 mol.) of α-chloroacetyl chloride in 25 ml. of ether. The reaction mixture is stirred at 25° for one hour then filtered. The filtrate is concentrated under reduced pressure to give 3-(2-chloroacetyl)-1,3-bis(2-cyano-5-trifluoromethylphenyl)triazene as an oil which crystallizes upon trituration with isopropyl ether, m.p. 98°–100°.

EXAMPLE 21

When an equivalent amount of α-bromoacetyl bromide is used in place of α-chloroacetyl chloride in the procedure of Example 20, 3-(2-bromoacetyl)-1,3-bis(2-cyano-5-trifluoromethylphenyl)triazene is obtained.

EXAMPLE 22

A solution of 4.06 g. (0.027 mol.) of 3-carbomethoxypropionyl chloride in 20 ml. of ether is added dropwise to a solution of 10.0 g. (0.026 mol.) of 1,3-bis(2-cyano-5-trifluoromethylphenyl)triazene and 1.39 g. (0.029 mol.) of 50% sodium hydride prepared as described above. The reaction mixture is stirred at 25° for 12 hours then filtered. The filtrate is concentrated to give a gum which is dissolved in hot ether. The ether solution is treated with decolorizing carbon, cooled and hexane is added to precipitate 3-(3-methoxycarbonylpropionyl)-1,3-bis(2-cyano-5-trifluoromethylphenyl)-triazene, m.p. 101°–103°.

EXAMPLE 23

A solution of 1.1 g. (0.016 mol.) of sodium nitrite in 8 ml. of water is added dropwise to a cooled (0°) slurry of 3.0 g. (0.016 mol.) of 2-cyano-5-trifluoromethylaniline in 3.6 ml. of concentrated sulfuric acid and 3.6 ml. of water. After addition, the diazonium solution is poured into 75 ml. of ethanol containing 3 g. of p-aminobenzoic acid and the precipitate which immediately forms is collected and washed with water to give 1-(4-carboxyphenyl)-3-(2-cyano-5-trifluoromethyl-phenyl)triazene, m.p. 192°–195° (ether).

EXAMPLE 24

When an ester listed below:
malonic acid mono-butyl ester
succinic acid mono-propyl ester
glutaric acid mono-methyl ester
adipic acid mono-ethyl ester
is refluxed on a steam bath with an excess amount of thionyl chloride, the following acid chlorides are obtained:
2-carbobutoxyacetyl chloride
3-carbopropoxypropionyl chloride
4-carbomethoxybutyryl chloride
5-carbethoxyvaleryl chloride.

Substitution of an equivalent amount of an acid chloride listed above in the procedure of Example 22 for 3-carbomethoxypropionyl chloride gives the following compounds of this invention:
3-(2-butoxycarbonylacetyl)-1,3-bis(2-cyano-5-trifluoromethylphenyl)triazene
3-(3-propoxycarbonylpropionyl)-1,3-bis(2-cyano-5-trifluoromethylphenyl)triazene
3-(4-methoxycarbonylbutyryl)-1,3-bis(2-cyano-5-trifluoromethylphenyl)triazene
3-(5-ethoxycarbonylvaleryl)-1,3-bis(2-cyano-5-trifluoromethylphenyl)triazene.

EXAMPLE 25

A solution of 10.0 g. (0.026 mol.) of 1,3-bis(2-cyano-5-trifluoromethylphenyl)triazene, 6.0 g. (0.029 mol.) of N,N-dicyclohexylcarbodiimide and 5.1 g. (0.026 mol.) of 4-diethylaminobutyric acid hydrochloride in 800 ml. of methylene chloride is stirred at 25° for 12 hours. The reaction mixture is filtered and the filtrate is concentrated under reduced pressure to give a residue which is washed with ether and recrystallized from benzene to give 3-[4-(N,N-diethylamino)butyryl]-1,3-bis(2-cyano-5-trifluoromethylphenyl)-triazene hydrochloride.

The hydrochloride salt is dissolved in benzene or chloroform and carefully neutralized with dilute aqueous base to give 3-[4-(N,N-diethylamino)butyryl]-1,3-bis(2-cyano-5-trifluoromethylphenyl)triazene.

EXAMPLE 26

When an equivalent amount of 2-dimethylaminoacetic acid is substituted in the procedure of Example 25 for 4-diethylaminobutyric acid, 3-[2-(N,N-dimethylamino)acetyl]-1,3-bis(2-cyano-5-trifluoromethylphenyl)triazene is obtained as the final product.

EXAMPLE 27

A solution of 10.0 g. (0.026 mol.) of 1,3-bis(2-cyano-5-trifluoromethylphenyl)triazene and 1.8 g. of sodium hydride in 750 ml. of ether is added to a solution of 4.45 g. (0.026 mol.) of 3-bromopropionyl chloride in 50 ml. of ether. The reaction mixture is stirred for 12 hours at 25°, then filtered to remove the precipitate formed during the reaction. The filtrate is cooled to −10° and dimethylamine (0.026 mol.) is added. The mixture is cooled for 12 hours, concentrated in vacuo and the residue is washed with ether-hexane and dried in vacuo to give 3-[2-(N,N-dimethylamino)propionyl]-1,3-bis(2-cyano-5-trifluoromethylphenyl)triazene hydrobromide.

The hydrobromide salt is dissolved in benzene or chloroform and carefully neutralized with dilute aqueous base to give 3-[2-(N,N-dimethylamino)propionyl]-1,3-bis(2-cyano-5-trifluoromethylphenyl)triazene.

EXAMPLE 28

A solution of the sodium salt prepared from 10.0 g. (0.026 mol.) of 1,3-bis(2-cyano-5-trifluoromethylphenyl)-triazene and 1.4 g. (0.029 mol.) of sodium hydride in 700 ml. of ether is added dropwise to a solution of 4.65 g. (0.03 mol.) of succinyl chloride in 150 ml. of ether. The reaction mixture is stirred for 12 hours at 25°, filtered and the filtrate is concentrated in vacuo. The residue is washed with hexane, ether is added and the precipitate is removed by filtration. The volume is brought to 500 ml. with ether and a small amount of water is added. The mixture is stirred for 12 hours and the ethereal solution is dried (MgSO₄) and concentrated in vacuo to give 3-(3-carboxypropionyl)-1,3-bis(2-cyano-5-trifluoromethylphenyl)triazene.

EXAMPLE 29

Substitution of malonyl chloride, adipoyl chloride or glutaryl chloride in the procedure of Example 28 for succinyl chloride gives the following compounds of this invention as products, respectively:
3-(2-carboxyacetyl)-1,3-bis(2-cyano-5-trifluoromethylphenyl)triazene
3-(4-carboxybutyryl)-1,3-bis(2-cyano-5-trifluoromethylphenyl)triazene
3-(4-carboxyvaleryl)-1,3-bis(2-cyano-5-trifluoromethylphenyl)triazene.

EXAMPLE 30

| Ingredients | Amounts |
| --- | --- |
| 1,3-bis(2-cyano-5-trifluoromethylphenyl)triazene | 25 mg. |
| Calcium sulfate dihydrate | 150 mg. |
| Sucrose | 25 mg. |
| Starch | 15 mg. |
| Talc | 5 mg. |
| Stearic Acid | 3 mg. |

The sucrose, calcium sulfate dihydrate and 1,3-bis(2-cyano-5-trifluoromethylphenyl)triazene are thoroughly mixed and granulated with 10% gelatin solution. The wet granules are screened, dried and then mixed with the starch, talc and stearic acid, screened and compressed into a tablet.

EXAMPLE 31

| Ingredients | Amounts |
| --- | --- |
| 1,3-bis(2-cyano-5-trifluoromethylphenyl)triazene | 100 mg. |
| Magnesium stearate | 5 mg. |
| Lactose | 150 mg. |

The ingredients are mixed and filled into a hard gelatin capsule.

Similarly, the other substituted 1,3-diphenyltriazenes disclosed herein may be formulated into tablets and capsules by the procedures of Examples 30 and 31.

The compositions prepared as in Examples 30 and 31 are administered orally to a subject in need of anorectic and anti-obesity activity within the dose ranges given hereabove.

What is claimed is:
1. A compound of the formula:

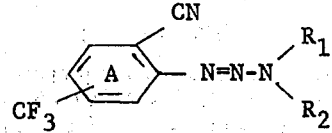

in which:
R₁ is phenyl, 4-carboxyphenyl or

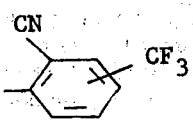

and
R₂ is hydrogen, formyl, α-chloroacetyl, α-bromoacetyl, alkanoyl, alkoxycarbonyl, alkoxycarbonylalkanoyl, carboxyalkanoyl, cyclopentylcarbonyl, cyclohexylcarbonyl, N-alkylcarbamoyl, N,N-dialkylcarbamoyl, N-phenylcarbamoyl, N-alkoxycarbonylcarbamoyl, or N,N-dialkylaminoalkanoyl, said alkyl and alkoxy having from one to four carbon atoms and said alkanoyl having from two to five carbon atoms.

2. A compound according to claim 1 in which R₂ is hydrogen, α-chloroacetyl, acetyl, ethoxycarbonyl, 3-methoxycarbonylpropionyl, N-methylcarbamoyl, N-propylcarbamoyl, N-phenylcarbamoyl or N-ethoxycarbonylcarbamoyl.

3. A compound according to claim 1 in which R₁ is 2-cyano-4-trifluoromethylphenyl or 2-cyano-5-trifluoromethylphenyl, the trifluoromethyl group of ring A is in the 4- or 5-position and R₂ is hydrogen or acetyl.

4. A compound according to claim 2 being the compound 1-(2-cyano-5-trifluoromethylphenyl)-3-phenyltriazene.

5. A compound according to claim 3 being the compound 1,3-bis(2-cyano-5-trifluoromethylphenyl)triazene.

6. A compound according to claim 3 being the compound 3-acetyl-1,3-bis(2-cyano-5-trifluoromethylphenyl)-triazene.

* * * * *